United States Patent
Wissel et al.

(10) Patent No.: US 11,721,439 B2
(45) Date of Patent: Aug. 8, 2023

(54) RESOLVING AND STEERING DECISION FOCI IN MACHINE LEARNING-BASED VASCULAR IMAGING

(71) Applicant: KONINKLIJKE PHILIPS N.V., Eindhoven (NL)

(72) Inventors: Tobias Wissel, Hamburg (DE); Hannes Nickisch, Hamburg (DE); Michael Grass, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 120 days.

(21) Appl. No.: 16/978,799

(22) PCT Filed: Mar. 4, 2019

(86) PCT No.: PCT/EP2019/055231
§ 371 (c)(1),
(2) Date: Sep. 8, 2020

(87) PCT Pub. No.: WO2019/170561
PCT Pub. Date: Sep. 12, 2019

(65) Prior Publication Data
US 2020/0411189 A1    Dec. 31, 2020

(30) Foreign Application Priority Data

Mar. 8, 2018 (EP) .................................... 18160717
May 30, 2018 (EP) .................................... 18175034

(51) Int. Cl.
*G16H 50/20*      (2018.01)
*G16H 50/30*      (2018.01)
(Continued)

(52) U.S. Cl.
CPC ............ *G16H 50/20* (2018.01); *G06T 7/0012* (2013.01); *G16H 30/40* (2018.01); *G16H 50/30* (2018.01);
(Continued)

(58) Field of Classification Search
None
See application file for complete search history.

(56) References Cited

U.S. PATENT DOCUMENTS 8,824,752 B1 *   9/2014   Fonte ..................... A61B 6/504
                                                                               382/126
9,471,989 B2   10/2016   O'Dell
(Continued)

FOREIGN PATENT DOCUMENTS

AU        2014364889 B2    6/2015
EP          0710851 A1    5/1996
(Continued)

OTHER PUBLICATIONS

Machine translation of JP-2017102869-A (Year: 2017).*
(Continued)

*Primary Examiner* — Vu Le
*Assistant Examiner* — Courtney Joan Nelson (57) ABSTRACT

A system (SY) for determining a relative importance of each of a plurality of image features ($F_n$) of a vascular medical image impacting an overall diagnostic metric computed for the image from an automatically-generated diagnostic rule. A medical kin image database (MIDB) includes a plurality of vascular medical images ($M_{1\ldots k}$). A rule generating unit (RGU) analyzes the plurality of C vascular medical images and automatically generates at least one diagnostic rule corresponding to a common diagnosis of a subset of the plurality of vascular medical images based on a plurality of image features common to the subset of vascular medical (Continued)

images. An image providing unit (IPU) provides a current vascular medical image (CVMI) including the plurality of image features. A diagnostic metric computation unit (DMCU) computes an overall diagnostic metric for the current vascular medical image by applying the at least one automatically-generated diagnostic rule to the current vascular medical image. A decision propagation unit (DPU) identifies, in the current vascular medical image, the relative importance of each of the plurality of image features on the computed overall diagnostic metric.

20 Claims, 2 Drawing Sheets

(51) Int. Cl.
  *G16H 30/40* (2018.01)
  *G06T 7/00* (2017.01)
(52) U.S. Cl.
  CPC ............... *G06T 2207/10101* (2013.01); *G06T 2207/20081* (2013.01); *G06T 2207/30101* (2013.01)

(56) References Cited

U.S. PATENT DOCUMENTS

| | | | | |
|---|---|---|---|---|
| 2015/0003701 A1* | 1/2015 | Klauschen | ............ | G06K 9/629 382/128 |
| 2015/0265162 A1* | 9/2015 | Lavi | ............ | G16H 50/30 600/408 |
| 2016/0235323 A1* | 8/2016 | Tadi | ............ | A61B 5/1128 |
| 2016/0235373 A1* | 8/2016 | Sharma | ............ | A61B 8/0891 |

FOREIGN PATENT DOCUMENTS

| | | | | |
|---|---|---|---|---|
| JP | H09238917 A | | 9/1997 | |
| JP | 2015211766 A | | 11/2015 | |
| JP | 2016500014 A | | 1/2016 | |
| JP | 2017102869 A | * | 6/2017 | |
| WO | 2015095282 A1 | | 6/2015 | |
| WO | 2016075331 A2 | | 5/2016 | |
| WO | WO-2016092779 A1 | * | 6/2016 | ......... G01N 21/8806 |

OTHER PUBLICATIONS

Luisa M Zintgraf, Taco S Cohen, Tameem Adel, Max Welling: "Visualizing Deep Neural Network Decisions: Prediction Difference Analysis", 2017; arXiv:1702.04595. (Year: 2017).*

Wojciech Samek, Thomas Wiegand, Klaus-Robert Müller: "Explainable Artificial Intelligence: Understanding, Visualizing and Interpreting Deep Learning Models", 2017; arXiv: 1708.08296 (Year: 2017).*

Gal et al: "Dropout as a Bayesian Approximation: Representing Model Uncertainty in Deep Learning"; Proceedings of the 33rd International Conference on Machine Learning, W&CP vol. 48, 2016.

Gurevich et al: "Learning Uncertainty in Regression Tasks by Deep Neural Networks"; Downloaded From https://arx.org/abs/1707.07287, Jan. 2018, 36 page Document.

Montavon et al: "Methds for Interpreting and Understanding Deep Neural Networks"; Digital Signal Processing 73 (2018) pp. 1-15.

Nemirovsky: "Imaging of High-Risk Plaque"; Cardiology 2003, vol. 100, pp. 160-175.

PCT/EP2019/055231 WO and Search Report, dated Jun. 13, 2019, 16 page Document.

Salakhutdinov et al: "Deep Boltzman Machines"; Proceedings of the 12th International Conference on Artifical Intelligence Statistics (AISTATS) 2009, pp. 448-455.

Sanchez et al: "Scaled Radial Axes for Interactive Visual Feature Selection: A Case Study for Analyzing Chronic Conditions"; Expert Systems With Applications, vol. 100 (2018) pp. 182-196.

Zeiler et al: "Visualizing and Understanding Convolutional Networks"; Computer Vision—ECCV, 2014, Springer Publishing, 2014, pp. 818-833.

* cited by examiner

RESOLVING AND STEERING DECISION FOCI IN MACHINE LEARNING-BASED VASCULAR IMAGING

CROSS-REFERENCE TO PRIOR APPLICATIONS

This application is the U.S. National Phase application under 35 U.S.C. § 371 of International Application No. PCT/EP2019/055231, filed on Mar. 4, 2019, which claims the benefit of European Patent Application No. 18160717.7, filed on Mar. 8, 2018 and European Patent Application No. 18175034.0, filed on May 30, 2018. These applications are hereby incorporated by reference herein.

FIELD OF THE INVENTION

The invention relates to the field of image guided therapy. More particularly it relates to decision making in the field of vascular imaging.

BACKGROUND OF THE INVENTION

Vascular imaging modalities such as intravascular ultrasound, i.e. IVUS or optical coherence tomography, i.e. OCT, play an increasingly important role in imaging coronary as well as peripheral vessels. Applications include the evaluation of coronary plaque as well as calcium burden, stenosis level characterization or imaging support in the context of stenting.

Data-driven decision support systems are also evolving in this domain. Increasingly this presents a need for the clinician to understand where automatically derived decision arise from, and where necessary, to interact with the decision-finding process. The present application addresses this and other needs.

The following documents are known in the field of the invention and in related fields:
[1] Dmitry Nemirovsky, Imaging of High-Risk Plaque, Cardiology 100:160-175; 2003.
[2] Grégoire Montavon, Wojciech Samek, and Klaus-Robert Müller: Methods for Interpreting and Understanding Deep Neural Networks Digital Signal Processing, 73:1-15, 2017.
[3] Zeiler, Matthew D., and Rob Fergus. Visualizing and understanding convolutional networks. Computer Vision-ECCV 2014. Springer. International Publishing, 818-833, 2014.
[4] R. R. Salakhutdinov and G. E. Hinton. Deep Boltzmann machines. In Proceedings of the International Conference on Artificial Intelligence and Statistics, volume 12, 2009.

Another document WO2015095282 discloses systems and methods for predicting coronary plaque vulnerability. One method includes acquiring anatomical image data of at least part of the patient's vascular system; performing, using a processor, one or more image characteristics analysis, geometrical analysis, computational fluid dynamics analysis, and structural mechanics analysis on the anatomical image data; predicting, using the processor, a coronary plaque vulnerability present in the patient's vascular system, wherein predicting the coronary plaque vulnerability includes calculating an adverse plaque characteristic based on results of the one or more of image characteristics analysis, geometrical analysis, computational fluid dynamics analysis, and structural mechanics analysis of the anatomical image data; and reporting, using the processor, the calculated adverse plaque characteristic.

SUMMARY OF THE INVENTION

Vascular imaging techniques such as IVUS or (coronary) computed tomography angiography, i.e. (C)CTA, play an increasingly important role in imaging coronary as well as peripheral vessels. Applications include the evaluation of coronary plaque as well as calcium burden, stenosis level characterization or imaging support in the context of stenting.

The advent of data-driven decision support systems in this domain generates the need for the clinician to understand where automatically-derived decision arise from, and where necessary, to interact with the decision-finding process. The higher and more abstract the decision level, the larger the need to understand the process.

In the particular example of plaque detection and risk scoring for e.g. acute coronary syndrome, i.e. ACS, an algorithm can be trained from data to detect certain image features, e.g. soft plaques and calcium, from intravascular images along the vessel-of-interest and join them into a risk score. In this case it may happen that image artefacts, e.g. originating from motion such as cardiac motion, contrast agent variations, existing stents or other implants remain unrecognized and erroneously impact the decision.

The invention provides a system for determining a relative importance of each of a plurality of image features of a vascular medical image impacting an overall diagnostic metric computed for the image from an automatically-generated diagnostic rule. The system includes a medical image database, a rule generating unit, an image providing unit, a diagnostic metric computation unit, and a decision propagation unit. The medical image database includes a plurality of vascular medical images. The rule generating unit analyzes the plurality of vascular medical images and automatically generates at least one diagnostic rule corresponding to a common diagnosis of a subset of the plurality of vascular medical images based on a plurality of image features common to the subset of vascular medical images. The image providing unit provides a current vascular medical image including the plurality of image features. The diagnostic metric computation unit computes an overall diagnostic metric for the current vascular medical image by applying the at least one automatically-generated diagnostic rule to the current vascular medical image. The decision propagation unit identifies, in the current vascular medical image, the relative importance of each of the plurality of image features on the computed overall diagnostic metric.

Automatically-generated rules that analyze vascular images to provide an overall diagnostic metric such as calcium burden, may e.g. be generated by a machine-learning process. In general the machine learning process weights various image features in order to arrive at the rule and then computes the overall diagnostic metric. However, the weighting of each feature is typically a hidden parameter, and consequently the relative importance of each of the image features that affect the diagnostic metric is not transparent. Known systems compute either only an overall diagnostic parameter for an image, or indicate high risk regions in the image, but do not indicate the relative importance of each feature in an image to the overall diagnostic parameter. In some instances such automatically-generated rules may erroneously identify image features with a high weighting, resulting in a high overall risk score for the image. Image artefacts originating from motion such as e.g.

cardiac motion, or a contrast agent variation, an existing stent, an implant or a bifurcation, may be incorrectly automatically identified in this manner. By identifying in the vascular medical image the relative importance of each of the plurality of image features on the computed overall diagnostic metric, the system advantageously allows a user to validate the underlying assumptions of the automatically-generated rule. A user will readily know from their own experience whether such motion artefacts, stents and so forth should indeed have the identified relative impact on the computed overall diagnostic metric.

In accordance with one aspect the diagnostic metric computation unit is further configured to receive user input from a user input device indicative of at least one of said plurality of image features and to either i) re-compute the overall diagnostic metric for the current vascular medical image by changing the relative importance of said at least one of said plurality of images features and re-applying the at least one diagnostic rule to the current vascular medical image or to ii) change the relative importance of said at least one of said plurality of image features and cause the rule generating unit to re-analyze the plurality of vascular medical images and to automatically generate a revised diagnostic rule corresponding to a common diagnosis of a selection of the vascular medical images based on a plurality of image features common to the selection of the vascular medical images, and to cause the diagnostic metric computation unit to compute a revised overall diagnostic metric for the current vascular medical image by applying the revised automatically-generated diagnostic rule to the current vascular medical image, and to cause the decision propagation unit to identify, in the current vascular medical image, the relative importance of each of the plurality of image features on the computed revised overall diagnostic metric.

Thus, in accordance with this aspect the system may allow a user to change the relative importance of e.g. a region of the image currently being analyzed and to either re-apply the same diagnostic rule and re-compute the overall diagnostic metric for the image, or to change the relative importance of e.g. a region of the image currently being analyzed and re-compute the diagnostic rule and re-compute the overall diagnostic metric for the image. For example, the user may indicate to the system that a region in the image corresponding to a stent, which has, erroneously, been identified as having a high impact on the originally-computed diagnostic metric, should not contribute to this metric at all, and in response to this the system is caused to so re-compute the overall diagnostic metric by neglecting any contribution to the metric by the stent.

In accordance with other related aspects a corresponding method and computer program product are also provided.

The invention therefore tackles one or more of the aforementioned needs by propagating the automatic decision back into relevance scores within the input image space. The relevance scores may be indicated by means of heat maps. These heat-map-like structures can be used to understand the decision, validate or reject it, or most importantly, provide a means of feedback for the clinician. The latter is achieved by image manipulations that reduce or increase the impact of certain image features on the decision. Heat-maps can either be used to directly modulate the input image or as a separate extra feedback channel to the system. Apart from standard feedforward decision systems, generative models with bidirectional inference constitute another means for imputing masked or modulated inputs and re-computing the desired outputs.

DETAILED DESCRIPTION OF THE INVENTION

In order to illustrate the principles of the present invention a system for determining a relative importance of each of a plurality of image features of a vascular medical image is described with particular reference to IVUS images. It is however to be appreciated that the system may alternatively be used with images from other imaging modalities, including but not limited to OCT, (C)CTA, or angiography, images.

As mentioned above, vascular imaging modalities such as IVUS or OCT play an increasing role in imaging coronary as well as peripheral vessels. Applications include the evaluation of the coronary plaque as well as calcium burden, stenosis level characterization or imaging support in the context of stenting.

The advent of data-driven decision support system in this domain generates the need for a clinician to understand where automatically derived decision arise from and to interact with decision-finding process if necessary. The higher and more abstract the decision level, the greater the need to understand the process. The present invention may also assist in meeting the increased requirements for formal documentation of diagnostic and therapeutic decision-making.

In the particular example of plaque detection and risk scoring for e.g. ACS, an algorithm trained from data to detect certain image features from intravascular images along the vessel-of-interest can join these local evidences into an overall risk score. Concretely, the detection and assessment of soft plaque patterns, as described in citation [1], their extent and distribution across the vessel tree, will substantially influence the ACS score. In this scenario, it may happen that image artefacts, e.g. originating from motion such as cardiac motion, contrast agent variations, existing stents or other implants remain unrecognized and erroneously impact the decision system. Additional certainty measures on the output often do not resolve the problem and provide no means for interaction between clinician and the support system. In other cases the support system might be insufficiently trained to cope with special data appearances, e.g. contrast drops, motion artefacts, unusual view from less experienced users. Those scenarios typically require repeated acquisitions or abandoning the support system, which is time-consuming or impossible in case of post hoc processing.

Figures 1, 2:
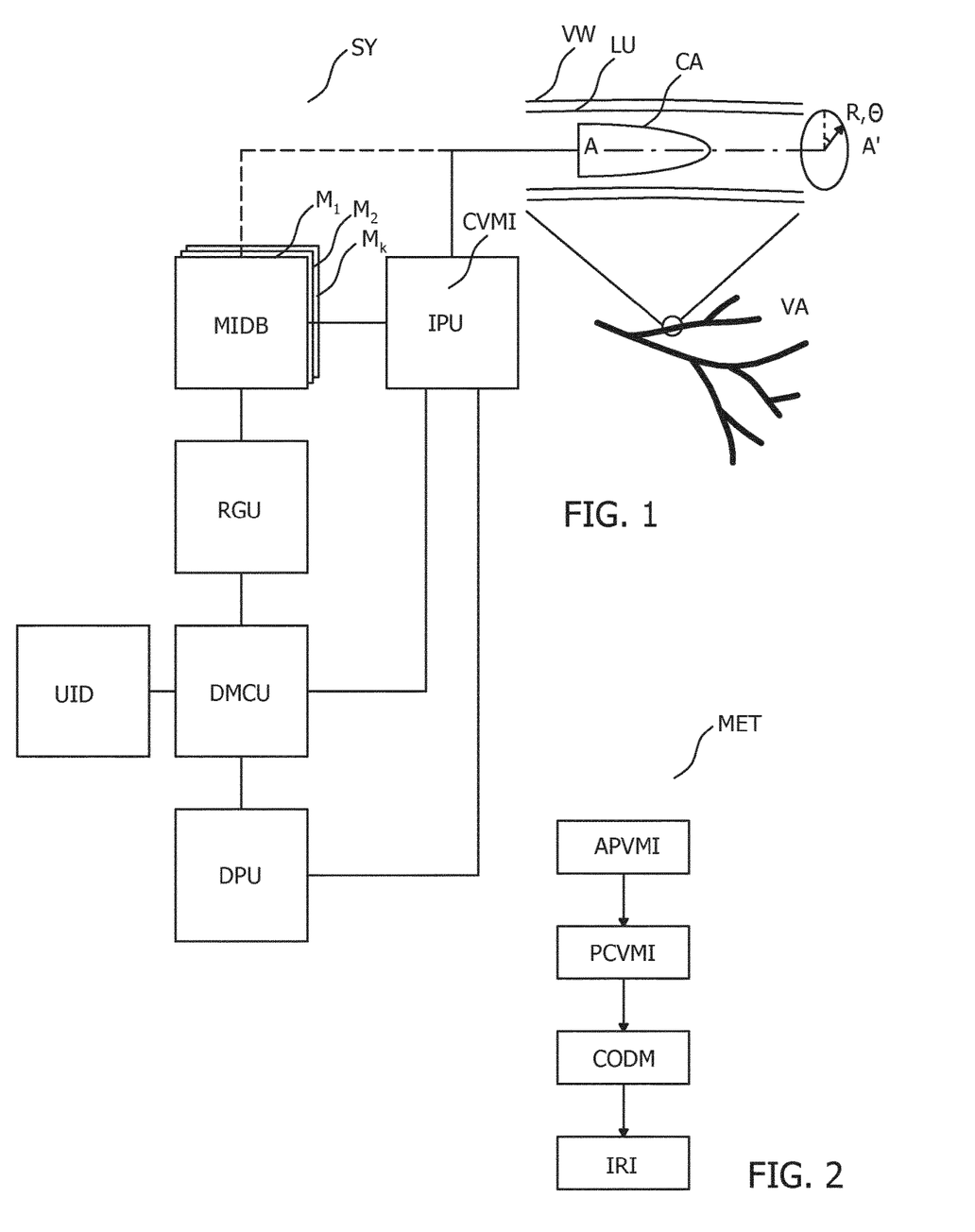
FIG. 1 illustrates a system SY for determining a relative importance of each of a plurality of image features $F_n$ of a vascular medical image impacting an overall diagnostic metric computed for the image from an automatically-generated diagnostic rule in accordance with some aspects of the invention.
FIG. 2 illustrates a method MET in accordance with some aspects of the invention.

FIG. 1 illustrates a system SY for determining a relative importance of each of a plurality of image features $F_n$ of a vascular medical image impacting an overall diagnostic metric computed for the image from an automatically-generated diagnostic rule in accordance with some aspects of the invention. System SY includes medical image database MIDB, rule generating unit RGU, image providing unit IPU, diagnostic metric computation unit DMCU, and decision propagation unit DPU. The functions of these items may in general be provided by computer-related products. More specifically the functions of items RGU, DMCU and DPU may be implemented by one or more processors, and the functions of units MIDB and IPU may be implemented by one or more memories. The memory(ies) may be supported or controlled by one or more processors.

With continued reference to FIG. 1, medical image database MIDB includes a plurality of vascular medical images $M_{1 \ldots k}$. In embodiments consistent with the present invention the images may for example be either i) IVUS, ii) OCT, iii) (C)CTA, or iv) angiography, images. The invention is however not limited to these examples. Rule generating unit RGU is configured to analyze the plurality of vascular medical images $M_{1 \ldots k}$ and to automatically generate at least one diagnostic rule corresponding to a common diagnosis of a subset of the plurality of vascular medical images based on a plurality of image features $F_n$ common to the subset of vascular medical images. Suitable techniques for analyzing such images are in general known from citations [1-4] above, and may in general include providing the at least one diagnostic rule by executing for example either a machine learning algorithm, a deep learning algorithm or an automatic intelligence algorithm. Image features $F_n$ may in general correspond to image intensities, or more specifically by way of non-limiting examples correspond to plaque, calcium, a presence of ruptured plaque, a thrombus in a lesion, a presence of fat in the plaque adjacent to a lumen, and/or include one or more of a computed lumen area, a computed plaque area, a computed lesion dimension, a computed distribution or proportion of calcium in a lesion.

With continued reference to FIG. 1, image providing unit IPU is configured to provide a current vascular medical image CVMI comprising the plurality of image features $F_n$. Current vascular medical image CVMI may be an image received from medical image database MIDB, or indeed an image received from another database such as a database within image providing unit IPU or a networked server, or indeed an image received from catheter CA in vasculature VA. Current vascular medical image CVMI may be a pre-recorded or a live image. Vasculature VA may be a portion of the vasculature of a human or animal body. The illustrated portion in FIG. 1 includes lumen LU that defines axis A-A', and which lumen LU has a corresponding vascular wall VW. Catheter CA may in the illustrated example be an IVUS or OCT imaging catheter that provides OCT or IVUS image data that is measured rotationally, as indicated by angle $\theta$, around axis A-A'. In the case of IVUS, the intensity of the data corresponds to the ultrasound reflectance of surrounding matter. In the case of OCT the data corresponds to interference between an optical irradiation beam and a reflected portion of the beam. By rotationally it is meant that the data is measured around a portion of angular direction $\theta$. Said data may for example be acquired from a fixed array of IVUS/OCT detector elements, said elements being arranged around angular direction $\theta$ with respect to catheter CA, or from a scanning or rotating IVUS/OCT detector wherein one or more detector elements, or a corresponding optical element, is rotated around angular direction $\theta$ with respect to catheter CA. Said data is typically acquired during a so-called "pullback" procedure in which catheter CA, which has previously typically been inserted in vasculature VA with the assistance of a guidewire, is subsequently pulled-back along the vasculature whilst acquiring data.

As illustrated by the dashed line interconnecting catheter CA and medical image database MIDB, catheter CA may also be used in a similar manner as described above to provide plurality of vascular medical images $M_{1 \ldots k}$ to medical image database MIDB. In one implementation mentioned above, current vascular medical image CVMI may be one of plurality of vascular medical images $M_{1 \ldots k}$. In another implementation vascular medical images $M_{1 \ldots k}$ may be acquired at an earlier point in time to current vascular medical image CVMI. In some implementations vascular medical images $M_{1 \ldots k}$ may be acquired from the same a vasculature as current vascular medical image CVMI whereas in other implementations vascular medical images $M_{1 \ldots k}$ may be acquired from a different vasculature to current vascular medical image CVMI. Vascular medical images $M_{1 \ldots k}$ may be acquired using the same, or a different, catheter to that which provides current vascular medical image CVMI. Vascular medical images $M_{1 \ldots k}$ may be acquired prior to current vascular medical image CVMI.

When system SY is used with alternative image types such as images provided by (C)CTA, or angiography, the origins of these images may also be as described above.

With continued reference to FIG. 1, diagnostic metric computation unit DMCU computes an overall diagnostic metric for the current vascular medical image CVMI by applying the at least one automatically-generated diagnostic rule to the current vascular medical image CVMI. By the term overall, it is intended that the plurality of image features have an impact on the diagnostic metric rather than simply one image feature affecting this metric. Non-limiting examples of the overall diagnostic metric include: a risk score corresponding to a risk of an acute coronary event such as ACS, calcium burden, a risk of peripheral vascular disease, a risk of coronary plaque, a risk of coronary vascular disease or a stenosis level characterization. Other overall diagnostic metrics may be computed in a similar manner.

Subsequently, decision propagation unit DPU identifies, in the current vascular medical image CVMI, the relative importance of each of the plurality of image features $F_n$ on the computed overall diagnostic metric. Thus, in contrast to simply identifying regions with e.g. high risk in the diagnostic image, the relative importance of each of the image regions on the computed high-risk score, is identified. This allows a user to determine the relative importance of key regions or aspects of the current image to the computed overall diagnostic metric, and consequently to validate their relative importance. In one example implementation the impact of each pixel in the current vascular medical image CVMI on the overall diagnostic metric for that image may be rated on a scale from 1 to 100, 100 being the sole factor that affects the computed overall diagnostic metric, and indicated as e.g. a color. Groups of pixels can be represented in a similar manner. This can be very beneficial when such diagnostic metrics are automatically generated since the transparency of the decision-making supports a user's confidence in the automatic decision-making and allows for the identification of results that do not fit with a user's own experience.

A preferred manner in which this relative importance can be indicated in the in the form of a heatmap overlaid on current vascular medical image. In this, image regions having a relatively higher impact on the overall diagnostic metric may be colored, e.g. red, whereas image regions having a relatively lower impact on the overall diagnostic metric may be transparent. Image regions having an intermediate impact may also be assigned various colors. By indicating the relative importance in this manner a user can readily validate the computed overall diagnostic metric. The relative importance of computed image features such as e.g. a lumen diameter and so forth may also be indicated in a similar manner. Clearly other forms of indication of the relative importance may alternatively be used, such as text and tabular indications on a display.

In one implementation the relative importance of each of the plurality of image features on the computed overall diagnostic metric may be determined based on a sensitivity of the computed overall diagnostic metric to a variation of each of the plurality of image features $F_n$. The sensitivity of the overall diagnostic metric may for example be computed by varying e.g. the intensity of each image feature by a predetermined percentage, and thereby used to identify the relative importance of regions of the current vascular medical image. The relative importance of computed image features such as e.g. a lumen diameter and so forth may also be varied by a predetermined percentage, e.g. by deforming the image using known image deformation techniques, in order to indicate their relative importance on the computed overall diagnostic metric in a similar manner.

In one implementation, a change in entropy of the computed overall diagnostic metric may be computed as a result of varying the plurality of image features Fn. This change in entropy, or more specifically the information gain as a result of changing the relative importance of the image features may provide an alternative indication of the relative importance of the image features on the computed overall diagnostic metric.

In one implementation the diagnostic metric computation unit DMCU is further configured to compute a measure of uncertainty of the overall diagnostic metric for the current vascular medical image. One method of computing the uncertainty is by training an additional network to predict the error of its own prediction. A suitable technique for this is described in document "Learning uncertainty in regression tasks by artificial neural networks" by Pavel Gurevich and Hannes Stuke, 20 Jan. 2018, arXiv:1707.07287, published online at https://arxiv.org/abs/1707.07287. An alternative method of computing the uncertainty is described in document "Dropout as a Bayesian Approximation: Representing Model Uncertainty in Deep Learning" by Yarin Gal and Zoubin Ghahramani, 4 Oct. 2016, arXiv:1506.02142, published online at https://arxiv.org/abs/1506.02142. In this latter method, uncertainty is computed using dropout and a Monte-Carlo estimate of the mean predictions and its variance. This approach uses an ensemble of weak rules. In a similar manner to the identification of the relative importance of each of the plurality of image features $F_n$ on the computed overall diagnostic metric, the decision propagation unit DPU may then identify the relative importance of each image feature to the uncertainty of the overall diagnostic metric in the current vascular medical image CVMI. This uncertainty may also support a user in validating the result of the automatically-generated rule. The user may for instance see that a particular image feature has a high impact on the computed overall diagnostic metric but that its uncertainty is very high. This may alert a user to consider to, as described below, change, or even neglect the contribution of this image feature to the computed overall diagnostic metric and to re-compute the metric. As described below, the system may alternatively perform this re-computation automatically.

As mentioned above, in one implementation system SY may additionally receive user input. The user input may be used to revise the diagnostic rule, and/or to re-compute the overall diagnostic metric. This implementation may thus allow a user to guide the creation of an improved diagnostic rule, and/or correct the diagnostic metric based on the user's own experience. In one instance diagnostic metric computation unit DMCU of system SY is further configured to receive this user input from a user input device UID. The user input is indicative of at least one of said plurality of image features $F_n$ and the diagnostic metric computation unit is configured to, based on said user input, re-compute the overall diagnostic metric for the current vascular medical image CVMI by changing the relative importance of said at least one of said plurality of images features $F_n$ and re-applying the at least one diagnostic rule to the current vascular medical image CVMI. The user input may for example indicate an image feature $F_n$ that corresponds to one or more image artefacts. Such image artefacts may include, for example, cardiac motion, a contrast agent variation, an existing stent, an implant, a bifurcation and so forth. Such image features may erroneously be determined, via the automatically-generated rule, as having a high relative importance on the computed overall diagnostic metric. A user may therefore manually change the relative importance of such features based on their own experience and thereby correct the diagnostic metric.

A user may provide this user input via user input device UID in FIG. 1 such as a pointer, a mouse, a keyboard and so forth. User input device UID may be used to define a region of the current vascular medical image CVMI provided by the image providing unit IPU. A user may for example identify the outline of a high relative-importance image feature in the current vascular medical image. System SY may facilitate this by for example automatically providing contours surrounding image features that have a relative importance that exceeds a predetermined threshold, wherein the user may select the image contour to provide the user input.

Changing the relative importance of said at least one of said plurality of image features $F_n$ may for instance mean increasing or decreasing or even neglecting the relative importance of said at least one of said plurality of image features $F_n$ When rule generating unit RGU automatically generates the at least one diagnostic rule by weighting each of the plurality of image features $F_n$; changing the relative importance of said at least one of said plurality of image features $F_n$ may include changing a weight of said at least one of said plurality of image features $F_n$.

In another instance the user input may be used to change the relative importance of at least one of the plurality of image features $F_n$ and cause the rule generating unit RGU to re-analyze the plurality of vascular medical images $M_{1 \ldots k}$ and to automatically generate a revised diagnostic rule corresponding to a common diagnosis of a selection of the vascular medical images $M_{1 \ldots k}$ based on a plurality of image features common to the selection of the vascular medical images $M_{1 \ldots k}$, and to cause the diagnostic metric computation unit to compute a revised overall diagnostic metric for the current vascular medical image CVMI by applying the revised automatically-generated diagnostic rule to the current vascular medical image CVMI, and to cause the decision propagation unit DPU to identify, in the current vascular medical image CVMI, the relative importance of each of the plurality of image features $F_n$ on the computed revised overall diagnostic metric. By so revising the diagnostic rule and re-computing the diagnostic metric an even more accurate diagnostic metric may be obtained because errors in the automatically-generated rule may be reduced.

In another implementation a method of determining a relative importance of each of a plurality of image features $F_n$ of a vascular medical image impacting an overall diagnostic metric computed for the image from an automatically-generated diagnostic rule; is provided. With reference to FIG. 2, which illustrates a method MET in accordance with some aspects of the invention, the method MET includes:

analyzing APVMI a plurality of vascular medical images $M_{1 \ldots k}$ and automatically generating at least one diagnostic rule corresponding to a common diagnosis of a subset of the vascular medical images based on a plurality of image features common to the subset of the vascular medical images;

providing PCVMI a current vascular medical image CVMI comprising the plurality of image features $F_n$;

computing CODM an overall diagnostic metric for the current vascular medical image CVMI by applying the at least one automatically-generated diagnostic rule to the current vascular medical image CVMI; and identifying IRI, in the current vascular medical image CVMI, the relative importance of each of the plurality of image features $F_n$ on the computed overall diagnostic metric.

Method MET may include additional steps that implement one or more of the functions described in relation to the items described in relation to FIG. 1 above. Moreover, method MET may be stored as instructions on a computer program product, which instructions, when executed on a computer, cause the computer to carry out the method MET.

Figure 3:
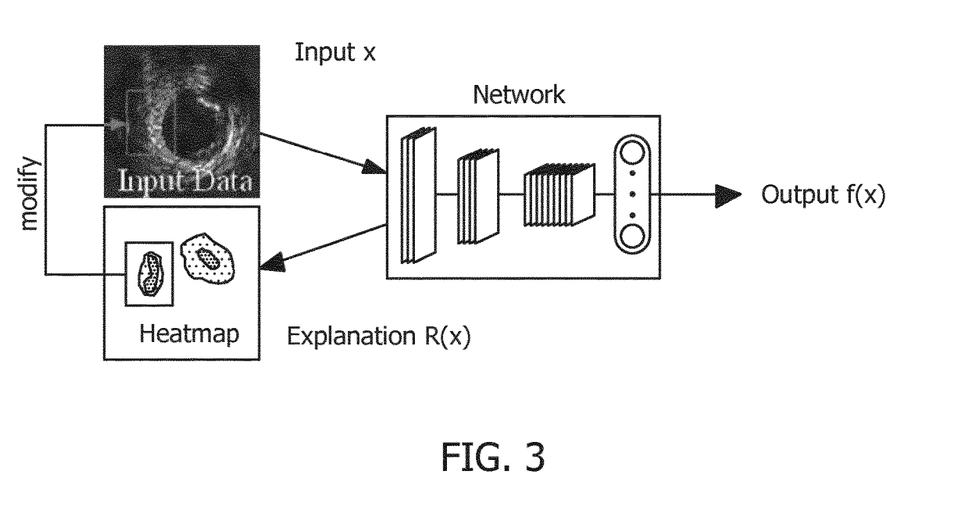
FIG. 3 illustrates an exemplary system in which a network makes predictions and interpretations using IVUS image data and outputs it to a user in the form of calcium scores.

The invention thus tackles one or more of the aforementioned needs by first propagating the automatic decision back into relevance scores within the input image space. A simple example of such a relevance score would be a sensitivity measure in a deterministic setting or an entropy difference in a probabilistic setting. Heat-maps can be used to visualize, communicate, document and understand the decision, and later to validate, reshape or reject it, or most important provide a means of feedback for the clinician—see FIG. 3.

Figure 4:
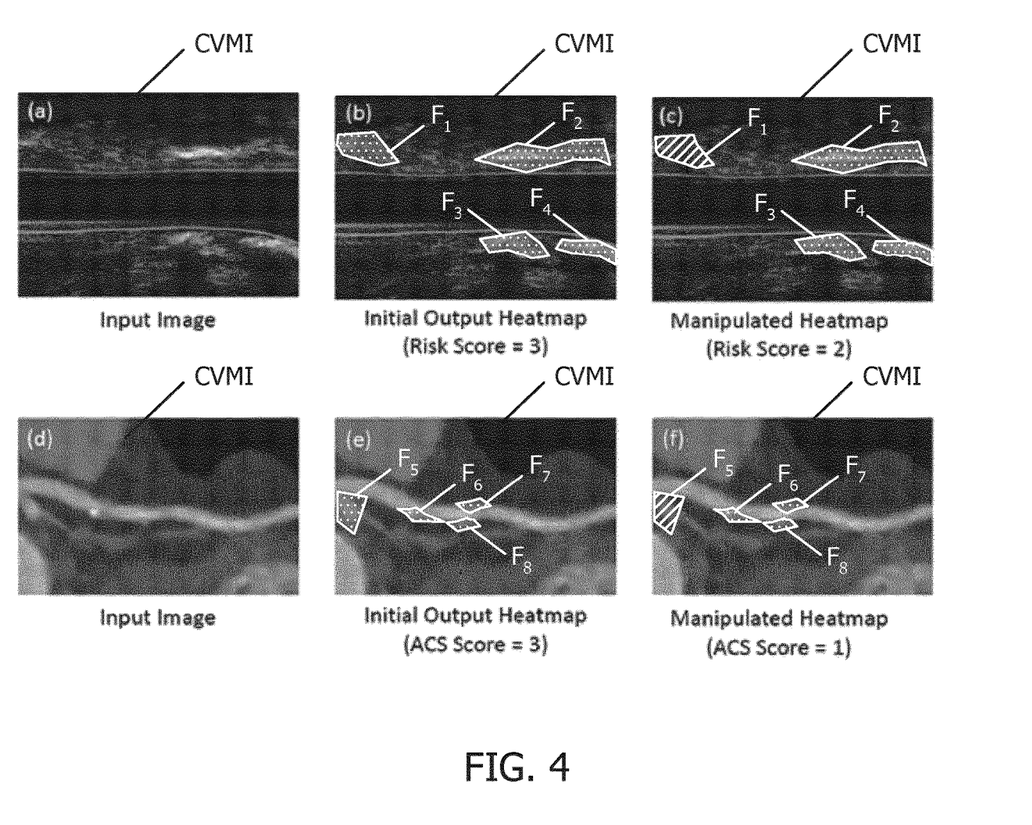
FIG. 4 illustrates exemplary relevance heat-maps that are used to feed information back into the system with a view to potentially correcting decisions after re-running an evaluation of the images, on (a-c) IVUS images, and (d-f) on coronary CTA images.

The latter is achieved by image manipulations that reduce or increase the impact of certain image features on the decision—see FIG. 4. Using relevance backpropagation, decision foci in the image domain can be identified, bottom image with red foci. While the right focus is a correctly detected calcium spot the left focus has been erroneously detected and drives the calcium score high by mistake. For focus steering via feedback interface, the user can modify the input based on this relevance, e.g. intensity modulation or erasing image features, and rerun the analysis with re-directed focus to possibly arrive at a different overall estimate—FIG. 3 adapted from citation [1].

Main Components:

Vascular Imaging: Input information is generated by one or more vascular imaging methods such as IVUS, OCT, CCTA, angiography etc. The information is provided as N-dimensional images which can in theory be examined manually or automatically to evaluate the risk for acute coronary events, calcium burden, peripheral vascular disease or others.

Decision Support System: The raw data is input into a decision support system, which takes the aforementioned image information as an input and provides a disease risk score and possibly a measure of uncertainty as an output.

Although the invention may primarily focus on such high level support with more complex reasoning, the application range may also be extended to lower level systems. An example would be the detection of certain plaque patterns such as e.g. the napkin-ring pattern for coronary high risk plaque, where the system would internally look for certain textures in the data to identify the pattern. Generally, the system is acting as black box, the behavior of which has been learned in a data-driven manner earlier.

Relevance Propagation Module: Once a decision is received at the output, the relevance propagation module can be triggered to propagate the decision back into the original image space. In an implementation of the invention, this would result in heat-map-like images in the same format as the input data. Since the decision of the support system was the only input to this module, the heat-map will contain only indications of which information in which regions has been used to arrive at this decision—see FIG. 3. Possible implementations for this module are system-specific and are presented in citation [2] or citation [3].

FIG. 4 illustrates exemplary relevance heat-maps that are used to feed information back into the system with a view to potentially correcting decisions after re-running an evaluation of the images, on (a-c) IVUS images, and (d-f) coronary CTA images. With reference to FIG. 4 (a-c) a system is trained on IVUS images to output a risk score based on the overall calcium burden in a vessel (a). The system generates a high risk score of e.g. 3 and provides a heat-map of decision foci within the image marking predominantly very bright segments (b). The user is of the opinion that the first segment should not be recognized as calcium and therefore erroneously increases the score. The segment is therefore downrated by making use of the heat-map (e.g. scale down the intensity in this focal area). This yields indeed a lower overall score (c). With reference to FIG. 4 (d-f), a similar scenario using coronary CTA data is described. The system predicts a high ACS score based on high risk plaque and calcium features (d). The system is mistaken with the first high focus segment which is in fact a bifurcation (e). The user decides to mask that region to be not part of the region. The mask can be applied to the input data or be used as an additional input channel to the system that would notify the system of a user-defined low priority in this area (f).

Feedback Module: The optional feedback module closes the loop to complete the interactive system. Given the heat-map, the feedback module provides an interface for the clinician to change the handling of the input. By manipulation of the heat-map, the attention focus of the decision support system can be steered. The human observer can downgrade regions which have been erroneously assigned a high relevance, e.g. attenuate the focus. This could result in masking or intensity modulating the input directly, or could be realized using an additional input channel to the decision system which indirectly notifies the system of a varying user-defined relevance in the input image. Examples for false high focus regions in the plaque scenario are: stents or other implants that may be interpreted as calcium, unusually high concentration of contrast agent, motion or other artefacts. Equally, upgrading of certain regions is also possible, e.g. generate focus. Examples include poor contrast regions that were not sufficiently taken into account, shadowing in ultrasound application etc.

After manipulation the transformed heat-map is used for re-weighting the input, directly or indirectly, and submitting the input once more to the decision system.

The decision support system is typically implemented by feedforward architectures. Alternatively, (probabilistic) generative models with bidirectional inference constitute another means for imputing masked inputs or exploit modulations to form prior information for the repeated inference process as discussed in citation [4].

For interventional applications, the feedback module interface can be realized via e.g. touch input, where the clinician can manipulate the heat-map and steer the foci using user-generated commands such as gestures. Re-focusing and additional user input can also be used to automatically improve the decision support system to avoid similar re-focusing cases over long-term.

The invention is relevant for applications that involve vascular imaging such as IVUS, CCTA or OCT. It may be used in interventional as well as post hoc applications. It is applicable to both coronary and peripheral vessels.

Any of the method steps disclosed herein may be recorded in the form of instructions which when executed on a processor cause the processor to carry out such method steps. The instructions may be stored on a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk—read only memory "CD-ROM", compact disk—read/write "CD-R/W", Blu-Ray™ and DVD.

In summary, a system for determining a relative importance of each of a plurality of image features of a vascular medical image impacting an overall diagnostic metric computed for the image from an automatically-generated diagnostic rule has been provided. The system includes a medical image database, a rule generating unit, an image providing unit, a diagnostic metric computation unit, and a decision propagation unit. The medical image database includes a plurality of vascular medical images. The rule generating unit analyzes the plurality of vascular medical images and automatically generates at least one diagnostic rule corresponding to a common diagnosis of a subset of the plurality of vascular medical images based on a plurality of image features common to the subset of vascular medical images. The image providing unit provides a current vascular medical image including the plurality of image features. The diagnostic metric computation unit computes an overall diagnostic metric for the current vascular medical image by applying the at least one automatically-generated diagnostic rule to the current vascular medical image. The decision propagation unit identifies, in the current vascular medical image, the relative importance of each of the plurality of image features on the computed overall diagnostic metric.

Various embodiments and options have been described in relation to system SY, and it is noted that the various embodiments may be combined to achieve further advantageous effects.

The invention claimed is:

1. A system for determining a relative importance of image features of a vascular medical image, the system comprising:
   a medical image database comprising a plurality of vascular medical images; and
   at least one processor configured to:
     analyze the plurality of vascular medical images and automatically generate at least one diagnostic rule corresponding to a common diagnosis of a subset of the plurality of vascular medical images based on a plurality of image features common to the subset of vascular medical images,
     receive a current vascular medical image comprising the plurality of image features,
     compute an overall diagnostic metric for the current vascular medical image by applying the at least one automatically-generated diagnostic rule to the current vascular medical image,
     identify, in the current vascular medical image, a relative importance of each of the plurality of image features to the computed overall diagnostic metric by backpropagation of the computed overall diagnostic metric into contribution of each of the plurality of image features to the computation of the computed overall diagnostic metric, and
     provide the current vascular medical image including an indication of the relative importance of each of the plurality of image features in the current vascular medical image.

2. The system according to claim 1, wherein the at least one processor is further configured to generate the at least one diagnostic rule by executing either a machine learning algorithm, a deep learning algorithm, or an automatic intelligence algorithm.

3. The system according to claim 1, wherein the overall diagnostic metric is a risk score corresponding to a risk of an acute coronary event, a risk of peripheral vascular disease, a risk of coronary plaque, a risk of coronary vascular disease, or a stenosis level characterization.

4. The system according to claim 1, wherein the at least one processor is further configured to identify the relative importance of each of the plurality of image features to the computed overall diagnostic metric in a form of a heatmap.

5. The system according to claim 1, wherein the at least one processor is further configured to:
   receive user input from a user input device indicative of at least one of the plurality of image features,
   either i) re-compute the overall diagnostic metric for the current vascular medical image by changing the relative importance of the least one of the plurality of image features and re-applying the at least one diagnostic rule to the current vascular medical image or to
   ii) change the relative importance of the at least one of the plurality of image features, re-analyze the plurality of vascular medical images to automatically generate a revised diagnostic rule corresponding to a common diagnosis of a selection of the vascular medical images based on a plurality of image features common to the selection of the vascular medical images, compute a revised overall diagnostic metric for the current vascular medical image by applying the revised automatically-generated diagnostic rule to the current vascular medical image, and identify, in the current vascular medical image, the relative importance of each of the plurality of image features to the computed revised overall diagnostic metric.

6. The system according to claim 5, wherein to change the relative importance of the at least one of the plurality of image features, the at least one processor is further configured to increase, decrease, or neglect the relative importance of the at least one of the plurality of image features.

7. The system according to claim 5, wherein the at least one processor is further configured to automatically generate the at least one diagnostic rule by weighting each of the plurality of image features and changing the relative importance of the at least one of the plurality of image features by changing a weight of the at least one of the plurality of image features.

8. The system according to claim 5, wherein the user input device is configured to define a region of the current vascular medical image.

9. The system according to claim 5, wherein the at least one of the plurality of image features corresponds to one or more image artefacts.

10. The system according to claim 1, wherein the at least one processor is further configured to identify, in the current vascular medical image, the relative importance of each of the plurality of image features to the computed overall diagnostic metric based on either i) a sensitivity of the computed overall diagnostic metric to a variation of each of the plurality of image features or ii) a change in entropy of the computed overall diagnostic metric resulting from a variation of each of the plurality of image features.

11. The system according to claim 1, wherein the plurality of image features corresponds to one or more of plaque, calcium, a presence of ruptured plaque, a thrombus in a lesion, a presence of fat in a plaque region adjacent to a lumen, and/or includes one or more of a computed lumen area, a computed plaque area, a computed lesion dimension, a computed distribution, or proportion of calcium in a lesion.

12. The system according to claim 1, wherein the plurality of vascular medical images and the current vascular medical image are either i) IVUS, ii) OCT, iii) (C)CTA, or iv) angiography images.

13. The system according to claim 1, wherein the at least one processor is further configured to:
compute a measure of uncertainty of the overall diagnostic metric for the current vascular medical image, and
identify said uncertainty in the current vascular medical image.

14. The system according to claim 1, wherein the backpropagation propagates the overall diagnostic metric back into a relevance score for each of the image features, the relevance score indicating relevance of the corresponding image feature to the computation of the overall diagnostic metric.

15. The system according to claim 1, wherein the at least one processor is further configured to:

based on the backpropagation of the computed overall diagnostic metric, detect an error in the identified relative importance of an image feature of the plurality of image features to the overall diagnostic metric;
modify the relative importance of the image feature based on the error; and
re-compute the overall diagnostic metric based on the modified relative importance of the image feature.

16. A method of determining a relative importance of image features of a vascular medical image, the method comprising:
analyzing a plurality of vascular medical images and automatically generating at least one diagnostic rule corresponding to a common diagnosis of a subset of the vascular medical images based on a plurality of image features common to the subset of the vascular medical images;
providing a current vascular medical image comprising the plurality of image features;
computing an overall diagnostic metric for the current vascular medical image by applying the at least one automatically-generated diagnostic rule to the current vascular medical image;
identifying, in the current vascular medical image, the relative importance of each of the plurality of image features to the computed overall diagnostic metric by backpropagating the computed overall diagnostic metric into contribution of each of the plurality of image features to the computation of the computed overall diagnostic metric; and
providing the current vascular medical image including an indication of the relative importance of each of the plurality of image features in the current vascular medical image.

17. The method according to claim 16, further comprising:
based on the backpropagation of the computed overall diagnostic metric, detecting an error in the identified relative importance of an image feature of the plurality of image features to the overall diagnostic metric;
modifying the relative importance of the image feature based on the error; and
re-computing the overall diagnostic metric based on the modified relative importance of the image feature.

18. A non-transitory computer-readable storage medium having stored a computer program comprising instructions, which, when executed by a processor, cause the processor to:
analyze a plurality of vascular medical images to automatically generate at least one diagnostic rule corresponding to a common diagnosis of a subset of the vascular medical images based on a plurality of image features common to the subset of the vascular medical images;
receive a current vascular medical image comprising the plurality of image features;
compute an overall diagnostic metric for the current vascular medical image by applying the at least one automatically-generated diagnostic rule to the current vascular medical image;
identify, in the current vascular medical image, the relative importance of each of the plurality of image features to the computed overall diagnostic metric by backpropagation of the computed overall diagnostic metric into contribution of each of the plurality of image features to the computation of the computed overall diagnostic metric; and provide the current vascular medical image including an indication of the relative importance of each of the plurality of image features in the current vascular medical image.

19. The A non-transitory computer-readable storage medium according to claim 18, wherein the backpropagation propagates the overall diagnostic metric back into a relevance score for each of the image features, the relevance score indicating relevance of the corresponding image feature to the computation of the overall diagnostic metric.

20. The A non-transitory computer-readable storage medium according to claim 18, wherein, the instructions, when executed by a processor, further cause the processor to:
   based on the backpropagation of the computed overall diagnostic metric, detect an error in the identified relative importance of an image feature of the plurality of image features to the overall diagnostic metric;
   modify the relative importance of the image feature based on the error; and
   re-compute the overall diagnostic metric based on the modified relative importance of the image feature.

\* \* \* \* \*